(12) United States Patent
Slininger et al.

(10) Patent No.: US 8,628,764 B2
(45) Date of Patent: Jan. 14, 2014

(54) BIOCONTROL OF STORAGE MALADIES OF POTATOES BY BACTERIAL ANTAGONISTS PRODUCED IN CO-CULTURE

(75) Inventors: Patricia J. Slininger, Metamora, IL (US); David A. Schisler, Morton, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/597,834

(22) Filed: Aug. 29, 2012

(65) Prior Publication Data

US 2012/0322658 A1  Dec. 20, 2012

Related U.S. Application Data

(62) Division of application No. 12/569,306, filed on Sep. 29, 2009, now Pat. No. 8,278,246.

(51) Int. Cl.
*A01N 63/00* (2006.01)
*C12N 1/20* (2006.01)
*C12Q 1/02* (2006.01)
*A61K 35/74* (2006.01)

(52) U.S. Cl.
USPC .................. 424/93.4; 435/252.1; 435/252.34; 435/42

(58) Field of Classification Search
None
See application file for complete search history.

(56) References Cited

U.S. PATENT DOCUMENTS 5,552,315 A * 9/1996 Slininger et al. ........... 435/253.3

OTHER PUBLICATIONS

Schisler et al (Phytopathology, vol. 67 No. 2, 1997 pp. 177-183).*

* cited by examiner

*Primary Examiner* — Robert A Zeman
(74) *Attorney, Agent, or Firm* — John Fado; Randall E. Deck; Lesley Shaw

(57) ABSTRACT

Bacterial compositions effective for inhibiting fungal diseases of potatoes and/or potato sprouting are produced by co-culture of two or more of *Pseudomonas fluorescens* (NRRL B-21133), *Pseudomonas fluorescens* biovar (NRRL B-21053), *Pseudomonas fluorescens* (NRRL B-21102) and *Enterobacter cloacae* (NRRL B-21050). Compositions produced by co-culture of these bacteria together in the same culture medium are significantly more effective for inhibiting fungi-induced diseases of potatoes and/or inhibiting sprouting of potatoes, than blends or mixtures of the same bacteria cultured separately.

7 Claims, 1 Drawing Sheet

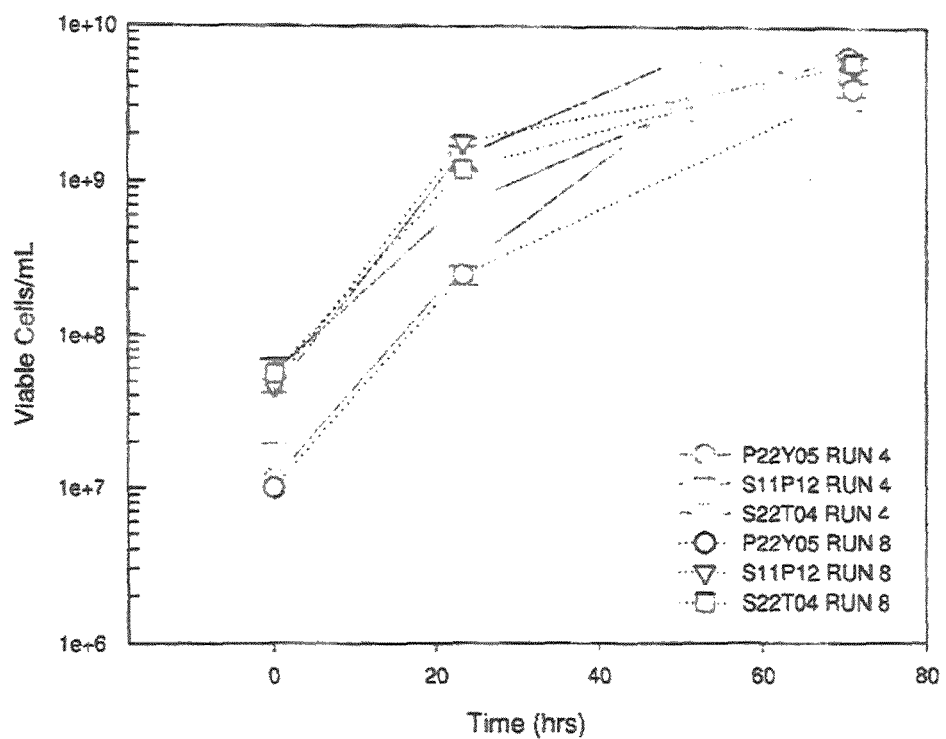

BIOCONTROL OF STORAGE MALADIES OF POTATOES BY BACTERIAL ANTAGONISTS PRODUCED IN CO-CULTURE

CROSS-REFERENCE TO RELATED APPLICATIONS

The present application is a division of copending U.S. patent application Ser. No. 12/569,306, filed Sep. 29, 2009, which is hereby incorporated by reference herein in its entirety.

BACKGROUND OF THE INVENTION

1. Field of the Invention

The present invention relates to the biological control of fungal potato diseases and/or potato sprout inhibition. More particularly, this invention relates to compositions of bacteria which are effective antagonists against fungal species responsible for *Fusarium* dry rot and other potato diseases which occur in the field or in postharvest storage.

2. Description of the Prior Art

The potato is the most important dicotyledonous source of human food, ranking as the fifth major food crop of the world. *Fusarium*-induced potato dry rot is an economically important problem of potatoes both in the field and in storage. Several species of the Fusaria induce this disease, however, *Gibberella pulicaris* (Fries) Sacc. (anamorph: *Fusarium sambucinum* Fuckel) is a major cause worldwide, especially in North America. *Fusarium* spp. can survive for years in field soil, but the primary inoculum is generally borne on seed tuber surfaces. The dry rot fungi infect potatoes via wounds in the periderm inflicted during harvesting or subsequent handling. In stored potatoes, dry rot develops most rapidly in high relative humidity (circa 70% and higher) and at 15°-20° C., but continues to advance at the coldest temperatures safe for potatoes. Although rots caused by *Fusarium* seldom reach epidemic proportions, the level of infected tubers in storage often reaches 60% or higher, with average losses estimated in the 10-20% range. In addition to destroying tissue, *F. sambucinum* can produce trichothecenes that have been implicated in mycotoxicoses of humans and animals.

The high value of the potato crop and the significant economic losses caused by potato dry rot have led to investigations of various methods to control the disease. Success has been attained by use of the fungicides, thiabendazole and 2-aminobutane, which are applied to tubers at harvest or at preplanting [Carnegie et al. 1990. Ann App. Biol. 116: 61-72; Leach, "Control of Postharvest *Fusarium* Tuber Dry Rot of White Potatoes," pages 1-7 In ARS-NE-55, U.S. Dep. Agric., Washington, D.C.]. However, strong concerns are being raised about the potential adverse impact of these chemicals on ground and surface water reservoirs and on the health of agricultural product workers and consumers. Also, thiabendazole-resistant strains of *F. sambucinum* have emerged in populations from severely dry-rotted tubers in North America and in Europe. Potato breeding programs have given increased attention to development of cultivars with resistance to *Fusarium* but most of the reported cultivars produced by these programs are resistant to only one or two of several *Fusarium* strains [Leach et al. 1981. Phytopathology 71(6): 623-629]

One alternative to chemical fungicides in controlling potato rot is the use of biological agents. Postharvest biological control systems of fruit have been actively investigated since the 1980's. These include iturins as antifungal peptides in biological control of peach brown rot with *Bacillus subtilis* [Gueldner et al. 1988. Journal of Agricultural and Food Chemistry 36:366-370]; postharvest control of blue mold on apples using *Pseudomonas* spp. isolate L-22-64 or white yeast isolate F-43-31 [Janisiewicz, 1987. Phytopathology 77:481-485]; control of gray mold of apple by *Cryptococcus laurentii* [Roberts, 1990. Phytopathology 80:526-530]; biocontrol of blue mold and gray mold on apples using an antagonistic mixture of *Pseudomonas* spp. and *Acremonium breve* [Janisiewicz, 1988. Phytopathology 78:194-198]; control of gray mold and reduction in blue mold on apples and pears with an isolate of *Pseudomonas capacia* and pyrrolnitrin produced therefrom [Janisiewicz and Roitman, 1988. Phytopathology 78:1697-1700]; postharvest control of brown rot in peaches and other stone fruit with the B-3 strain of *Bacillus subtilis* [Pusey and Wilson. 1984, Plant Disease 68:753-756; Pusey et al. 1988. Plant Disease 72:622-626; and U.S. Pat. No. 4,764,371 to Pusey et al.]; antagonistic action of *Trichoderma pseudokoningii* against *Botrytis cinerea* Pers. which causes the dry eye rot disease of apple [Tronsmo and Raa. 1977. Phytopathol. Z. 89:216-220]; and postharvest control of brown rot and *Alternaria* rot in cherries by isolates of *Bacillus subtilis* and *Enterobacter aerogenes* [Utkhede and Sholberg. 1986. Canadian Journal of Microbiology 963-967]. A review of biological control of postharvest diseases of fruits and vegetables is given by Wisniewski et al. [1992. HortScience 27:94-98].

More recently, significant progress has also been made in the isolation and development of bacteria agents for controlling diseases of potatoes. For instance, eighteen Gram-negative bacteria were originally discovered and developed as biocontrol agents to protect potatoes entering storage from *Fusarium* dry rot incited by *Gibberella pulicaris* [Schisler and Slininger. 1994. Selection and performance of bacterial strains for biologically controlling *Fusarium* dry rot of potatoes incited by *Gibberella pulicaris*. Plant Disease 8:251-255; Slininger et al. 1994 Two-dimensional liquid culture focusing: A method of selecting commercially promising microbial isolates with demonstrated biological control capability, in: M H Ryder, P M Stephens and G D Bowen (Eds.). Improving plant productivity with rhizosphere bacteria, 3rd international workshop on plant growth-promoting rhizobacteria, Adelaide, S. Australia, pp. 29-32. Glen Osmond, South Australia CSIRO Division of Soils; Slininger et al. 1996. Bacteria for the control of *Fusarium* dry rot of potatoes. U.S. Pat. No. 5,552,315; Schisler et al. 1997. Effects of antagonist cell concentration and two-strain mixtures on biological control of *Fusarium* dry rot of potatoes. Phytopathology 87:177-183; Schisler et al. 1998. Bacterial control of *Fusarium* dry rot of potatoes. U.S. Pat. No. 5,783,411], and these bacteria significantly reduced the level of dry rot disease in pilot trials (Schisler et al. 2000. Biological control of *Fusarium* dry rot of potato tubers under commercial storage conditions. American Journal of Potato Research 77:29-40). Top dry rot suppressive strains included *Pseudomonas fluorescens* biovar 5 (S11:P:12 NRRL B-21133 and P22:Y:05 NRRL B-21053, *Pseudomonas fluorescens* biovar 1 (S22:T:04 NRRL B-21102) and *Enterobacter cloacae* (S11:T:07 NRRL B-21050). All of these strains were also documented to suppress sprouting (Slininger et al. 2000. Biological control of sprouting in potatoes. U.S. Pat. No. 6,107,247; Slininger et al. 2003. Postharvest biological control of potato sprouting by *Fusarium* dry rot suppressive bacteria. Biocontrol Science and Technology 13:477-494), with *Pseudomonas fluorescens* S11:P:12 (NRRL B-21133) exhibiting the greatest efficacy, and *E. cloacae* S11:T:07 being the second most efficacious. In addition, the strains have been shown to suppress late blight incited by *Phytophthora infestans* US-8 mating type A2 in laboratory bioassays and small pilot simulations of commercial storage conditions with top performance shown by the following treatments: a mixture of four strains (comprised of S11:P:12+P22:Y:05+S22:T:04+ S11:T:07)>strain S22:T:04 used alone >strain S11:P:12 used alone [Slininger et al. 2007. Biological control of post-harvest late blight of potatoes. Biocontrol Science and Technology 17(5/6):647-663]. Most recently, we showed the ability of several of the dry rot antagonistic bacteria to suppress pink rot disease incited by *Phytophthora erythroseptica*, including S11:T:07 which exhibited the greatest efficacy and S22:T:04 exhibiting the third greatest efficacy (Schisler et al. 2007. Gram negative bacteria for reducing pink rot, dry rot, late blight, and sprouting potato tubers in storage. American Journal of Potato Research 84:115; Schisler et al. 2009. Bacterial antagonists, zoospore inoculums retention time and potato cultivar influence pink rot disease development. American Journal of Potato Research 86:102-11).

Several researchers have reported that mixtures of other microbial strains can enhance and/or improve the consistency of biological control (Pierson and Weller 1994. Use of mixtures of fluorescent pseudomonads to suppress take-all and improve the growth of wheat. Phytopathology 84:940-947; Duffy and Weller. 1995. Use of *Gaeumannomyces graminis* var. *graminis* alone and in combination with fluorescent *Pseudomonas* spp. to suppress take-all of wheat. Plant Disease 79:907-911; Duffy et al. 1996. Combination of *Trichoderma koningii* with fluorescent pseudomonads for control of take-all on wheat. Phytopathology 86:188-194; Janisiewicz. 1996. Ecological diversity, niche overlap, and coexistence of antagonists used in developing mixtures for biocontrol of post-harvest diseases of apples. Phytopathology 86:473-479; Leeman et al. 1996. Suppression of *Fusarium* wilt of radish by co-inoculation of fluorescent *Pseudomonas* spp. and root-colonizing fungi. European Journal of Plant Pathology 102: 21-31; de Boer et al. 1999. Combining fluorescent *Pseudomonas* spp. strains to enhance suppression of *Fusarium* wilt of radish. European Journal of Plant Pathology 105:201-210; Guetsky et al. 2001. Combining biocontrol agents to reduce the variability of biological control. Phytopathology 91:621-27; Krauss and Soberanis. 2001. Biocontrol of cocoa pod diseases with mycoparasite mixtures, Biological Control 22: 149-158; Hwang and Benson. 2002. Biocontrol of *Rhizoctonia* stem and root rot of poinsettia with *Burkholderia cepacia* and binucleate *Rhizoctonia*. Plant Disease 86:47-53; Cruz et. al. 2006. Exploiting the genetic diversity of *Beauveria bassiana* for improving the biological control of the coffee berry borer through the use of strain mixtures, Applied Microbiology and Biotechnology 71: 916-92. Preliminary research has shown that formulations containing multiple strains of the above-mentioned dry rot antagonists performed more consistently than individual strains did when subjected to thirty-two storage environments varying in potato cultivar, harvest year, potato washing procedure (microflora exposure), temperature, and storage time (Slininger et al. 2001. Combinations of dry rot antagonistic bacteria enhance biological control consistency in stored potatoes. Phytopathology 91:S83) However, despite these advances, the need remains for improved biological control agents for inhibiting fungal diseases of potatoes.

SUMMARY OF THE INVENTION

We have now discovered novel compositions of bacteria which are effective for inhibiting (reducing the incidence or severity of) fungal diseases of potatoes, and particularly fungal diseases of potatoes under storage conditions. The bacteria which comprise the compositions of this invention, specifically two or more of *Pseudomonas fluorescens* (NRRL B-21.13), *Pseudomonas fluorescens* biovar (NRRL B-21053), *Pseudomonas fluorescens* (NRRL B-21102) and *Enterobacter cloacae* (NRRL B-21050), have been previously described for the control of fungi-induced diseases of potatoes. However, we have unexpectedly discovered that when two or more of these bacteria are cultured together in the same culture medium, the resultant composition or co-culture is significantly more effective for inhibiting fungi-induced diseases of potatoes than blends of the same bacteria which have been cultured separately. In addition to their efficacy as biological control agents against fungi-induced diseases, the compositions also exhibit significantly greater control of sprouting in stored potatoes. The method of producing the bacterial antagonistic compositions comprises:

a) inoculating a culture medium with at least two bacteria selected from the group of *Pseudomonas fluorescens* (NRRL B-21133), *Pseudomonas fluorescens* (NRRL B-21053), *Pseudomonas fluorescens* (NRRL B-21102) and *Enterobacter cloacae* (NRRL B-21050), and incubating the inoculated medium containing said bacteria under conditions effective for their growth, and for a period of time effective to produce a co-culture thereof; and b) recovering the co-culture, a composition of bacteria effective for inhibiting fungal diseases of potatoes.

In accordance with this discovery, it is an object of this invention to provide novel compositions of bacteria which are superior antagonists of fungi responsible for fungi-induced potato diseases which occur in the field or in postharvest storage.

Another object of this invention is to provide novel compositions of bacteria which are superior antagonists of fungi responsible for *Fusarium* dry rot and other potato diseases which occur during postharvest storage.

Yet another object of this invention is to provide novel compositions of bacteria which exhibit significantly increased efficacy for inhibiting sprouting of potatoes during storage.

A further object of this invention is to provide novel method for producing compositions of bacteria which exhibit significantly increased efficacy for inhibiting fungi induced diseases of potatoes and inhibiting sprouting of stored potatoes.

These and other objects of the invention will become readily apparent from the ensuing description.

BRIEF DESCRIPTION OF THE FIGURES

FIG. 1 shows Growth of strains *P. fluorescens* strains S11: P:12, P22:Y:05, and S22:T:04 in duplicate co-culture fermentor runs as described in Example 1.

DEPOSIT OF BIOLOGICAL MATERIAL

Four bacterial antagonists described herein have been deposited under the terms of the Budapest Treaty in the Agricultural Research Service Culture Collection (NRRL), 1815 N. University St., Peoria, Ill. 61604, USA. These four bacteria were all originally described and deposited under the Budapest Treaty as set forth in Slininger et al., U.S. Pat. No. 5,552, 315, the contents of which are incorporated by reference herein. As described therein, *Pseudomonas fluorescens* biovar 5 isolate P22:Y:05 and *Enterobacter cloacae* S11:T:7 (which is also designated isolate S11:3:T:06) were deposited on Feb. 22, 1993 and were assigned deposit accession numbers NRRL B-21053 and NRRL B-21050, respectively. *Pseudomonas fluorescens* biovar 1 S22:T:04 was deposited on May 26, 1993, and was assigned deposit accession number (NRRL B-21102). *Pseudomonas fluorescens* biovar 5 isolate S11:P:12 was deposited on Aug. 30, 1993, and was assigned deposit accession number NRRL B-21133. The taxonomic characteristics for these deposited bacteria are described in the above mentioned U.S. Pat. No. 5,552,315.

DETAILED DESCRIPTION OF THE INVENTION

For purposes of this invention it is understood that the use of term *Fusarium* is intended to include both the sexual (teleomorphic) stage of this organism and also the asexual (anamorphic) stage, also referred to as the perfect and imperfect fungal stages, respectively. For example, the anamorphic stage of *Gibberella pulicaris* (Fries) Sacc. is known as *Fusarium sambucinum* (Fuckel). *Fusarium*-induced potato dry rot is a disease caused when a potato wound becomes inoculated with conidia produced by the imperfect form of this fungus.

The expression "superior antagonist" used herein in reference to a microorganism is intended to mean that the subject strain exhibits a degree of inhibition of fungal-induced potato disease (i.e. proliferation of an agent responsible for the disease) exceeding, at a statistically significant level, that of an untreated control.

The bacterial antagonist compositions of this invention are prepared from *Pseudomonas fluorescens* (NRRL B-21133), *Pseudomonas fluorescens* biovar (NRRL B-21053), *Pseudomonas fluorescens* (NRRL B-21102) and *Enterobacter cloacae* (NRRL B-21050), all of which were previously described in Slininger et al., U.S. Pat. No. 5,552,315. Although each of these isolates are effective for inhibiting fungi-induced diseases of potatoes, we have discovered that when to or more of these bacteria are cultured together in the same culture medium, the resultant composition or co-culture exhibits significant efficacy or inhibiting fungi-induced diseases of potatoes (i.e., they are superior antagonists). Moreover, the resultant co-cultures are significantly more effective for inhibiting fungi-induced diseases of potatoes than blends or mixtures of the same bacteria which are cultured separately and then subsequently combined or mixed. Further still, these compositions also exhibit significantly greater efficacy for inhibiting the sprouting of stored potatoes than blends or mixtures of the same bacteria which are cultured separately.

The bacterial antagonist compositions are produced by inoculating a culture medium with at least two of the above-mentioned bacteria of the group of *Pseudomonas fluorescens* (NRRL B-21133), *Pseudomonas fluorescens* (NRRL B-21053), *Pseudomonas fluorescens* (NRRL B-21102) and *Enterobacter cloacae* (NRRL B-21050), and incubating this inoculated medium containing the two or more bacteria under conditions effective for their growth, thereby producing a co-culture of the inoculated bacteria.

Propagation of the bacterial antagonists to prepare the composition or co-culture may be effected by culture under any conventional conditions and in media which promote their growth. Moreover, the different bacteria may be inoculated into the culture medium at the same or different times. However, we have discovered that the bacteria must be cultured together, that is, grown in the same culture medium in the same culture vessel or fermentor, for a sufficient period of time effective to increase the total concentration (i.e., population of cells) of the inoculated bacteria by at least approximately one order of magnitude (i.e., the total concentration of the bacteria must increase by at least a factor of approximately ten, measured from the total concentration of the bacteria in the culture medium at the time of their combination). The precise time period will of course vary with the culture conditions and may be readily determined by the skilled practitioner using conventional techniques to measure total cell numbers. Such techniques may include, for example microscopic counting, electronic particle counting (e.g., using a Coulter counter, serial dilution cultures, and optical cell density measurements of the culture medium. However, without being limited thereto, the minimum time of co-cultivation of the bacterial antagonists together, will typically be at least about 16 hours, which time should be sufficient to allow growth of all bacterial populations to increase by at least one order of magnitude. The amount of bacteria used in the inoculation is not critical, although the skilled practitioner will recognize that very small inoculums may require longer incubation times to produce sufficiently large quantities of co-culture for commercial applications. The amounts of the bacterial inoculums are typically approximately the same, however, greater amounts are preferably used for a slower growing bacterium in comparison to a fast growing bacterium.

A variety of known culture media are suitable for use herein for the culture and production of the bacterial antagonists of the co-culture. As a practical matter, and without being limited thereto, the bacteria antagonists are typically grown in aerobic liquid cultures on media which contain sources of carbon, nitrogen, and inorganic salts assimilable by the microorganism and supportive of efficient cell growth. Preferred carbon sources are hexoses such as glucose, but other assimilable sources include glycerol, amino acids, xylose, etc. Many inorganic and proteinaceous materials may be used as nitrogen sources in the growth process. Preferred nitrogen sources are amino acids an, urea, but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions. Similarly, suitable pH and temperature conditions are also variable. Cell growth of the disclosed bacteria can be achieved at temperatures between 1° and 40° C., with the preferred temperature being in the range of 15° and 30° C. The pH of the nutrient medium can vary between 4 and 9, but the preferred operating range is 6-8. The bacteria should be cultivated under aerobic conditions, preferably with agitation. The total time for the culture will be dependent on cultivation conditions, particularly the culture medium, temperature, and aeration. For the purpose of illustration and without being limited thereto, the co-culture is typically harvested 72 hr after inoculation when grown at 25° C., but may be as early as 20 to 24 hr, especially when grown under conditions leading to more rapid growth, such as higher temperatures (26-30° C.) or on certain media with ingredients that are more rapidly metabolized.

Following cultivation, the resultant co-culture of the bacterial antagonists is recovered for subsequent use. Although it is envisioned that crude preparations of the co-cultured bacteria in culture media may be used directly, in a preferred embodiment the bacteria are harvested and formulated as described herein below.

The bacterial antagonist compositions of this invention are effective for controlling, that is reducing the incidence or severity of fungal diseases of potatoes, in comparison to untreated controls. In a preferred embodiment, the compositions are effective for inhibiting fungal diseases of potatoes selected from the group consisting of Fusarium dry rot (caused by *Gibberella pulicaris*), pink rot (caused by *Phytophthora erythroseptica*, and late blight (caused by *Phytophthora infestans*). In addition, the compositions are also effective for control of (inhibiting) sprouting in stored potatoes, in comparison to untreated controls.

Following recovery, the bacterial co-culture may be optionally examined or screened to confirm efficacy in reducing the incidence and/or severity of disease in potatoes caused by the fungal agent of interest, particularly those described herein. A variety of bioassay techniques are suitable for use herein, such as described in the example hereinbelow, as well as in Slininger, U.S. Pat. No. 5,552,315. Alternatively or in addition, the bacterial co-culture may be optionally examined or screened to confirm efficacy in reducing the incidence of sprouting of potatoes during storage. Techniques suitable for use in the evaluation of sprout inhibition activity are described, for example, by Slininger et al., U.S. Pat. No. 6,107,247, the contents of which are incorporated by reference herein.

The bacterial compositions of the invention can be applied by any conventional method to the surfaces of potato tuber materials, to include without limitation whole potato tubers, potato tuber parts, or seed tubers. For example, they can be applied as an aqueous spray or dip, as a wettable powder, or as a dust. Formulations designed for these modes of application will usually include a suitable liquid or solid carrier together with other adjuvants, such as wetting agents, sticking agents and the like. Starch, polysaccharides, sodium alginate, cellulose, etc are often used in such formulations as carriers and sticking agents, and are suitable for use herein as well.

Where the desired effect is control of fungal diseases of potatoes, the expressions "an effective amount" and "a suppressive amount" are used herein in reference to that quantity of antagonist composition which is necessary to obtain a statistically significant reduction in the level of disease (measured as a decrease in the severity or the rate of incidence) relative to that occurring in an untreated control under suitable conditions of treatment as described herein. Without being limited thereto, the actual rate of application of a liquid formulation will typically vary from a minimum of about $1\times10^3$ to about $1\times10^{10}$ total viable cells/ml, and preferably from about $1\times10^5$ to about $1\times10^9$ total viable cells/m, assuming a mode of application which would achieve substantially uniform contact of at least about 90% of the potato surface. If the composition is applied as a solid formulation, the rate of application should be controlled to result in a comparable number of viable cells per unit area of potato surface as obtained by the aforementioned rates of liquid treatment.

Conversely, where the desired effect is inhibition of potato sprouting, the expressions "an effective amount" and "a suppressive amount" are used herein in reference to that quantity of the bacterial composition that is necessary to obtain a reduction in the amount of sprouting of the harvested potatoes during storage (and optionally disease proliferation) relative to that occurring in an untreated control under suitable conditions of treatment and storage as described herein. The rate of application of harvested co-culture will typically be in the range of 0.05 to 2 ml of harvested culture volume per 8 oz. potato. On a cell concentration basis, the rate of application should be at least about $1\times10^8$ total viable cells/ml and preferably at least $1\times10^9$ total viable cells/ml. Even better results are obtained at concentrations exceeding $1\times10^{10}$ total viable cells/ml. The optimum dosage will depend on a number of factors, such as the size of the potato, the specific bacteria in the co-culture, and the associated cultivation conditions of the bacterial compositions. The skilled practitioner will be able to determine the dosage of a given co-culture broth required for optimum expression of sprout and dry rot biocontrol activities.

It is envisioned that the temperatures at which the bacterial compositions are effective would range from about 5° C. to about 30° C. The preferred temperature range is 10 to 25° C., and the optimal range is considered to be 12° C. to 20° C. Therefore, the bacterial compositions can theoretically be applied at any time during the harvest, grading, or shipping process, or during the early stages of storage. Of course, potato tubers are susceptible to infection any time a wound occurs and the fungal disease agent is present. Therefore, the longer the delay between the tuber wounding and the treatment with the bacterial composition, the greater the chance the pathogen will successfully infect the tuber. Though we have previously demonstrated that delays of 4 h between wounding and treatment do not significantly affect antagonist performance, it is anticipated that longer delays may decrease the effectiveness of the treatment depending on methods of cell formulation and application.

The following example is intended only to further illustrate the invention and is not intended to limit the scope of the invention which is defined by the claims.

EXAMPLE 1

Materials and Methods
Bacterial Antagonists

Suppressive strains *Pseudomonas fluorescens* biovar 5 (S11:P:12 NRRL B-21133 and P22:Y:05 NRRL B-21053), *Pseudomonas fluorescens* biovar 1 (S22:T:04 NRRL R—21102) and *Enterobacter cloacae* (S11:T:07 NRRL B-21050) isolated by Schisler and Slininger (1994, ibid) were stored lyophilized in the ARS Patent Culture Collection (NCAUR, USDA, Peoria, Ill.). Stock cultures of bacteria in 10% glycerol were stored at −80° C. Glycerol stocks were streaked to ⅕ strength trypticase soy broth agar plates (⅕ TSA; Difco Laboratories, Detroit, Mich.) which were incubated 2-3 days at 25° C. ad refrigerated up to one week as a source of preculture inoculum.

Cultivation Medium

SDCL medium was prepared with 2 g/L each $K_2HPO_4$ and $KH_2PO_4$; minerals including 0.1 g/L $MgSO_4(7H_2O)$, 10 mg/L NaCl, 10 mg/L $FeSO_4(7H_2O)$, 4.4 mg/L $ZnSO_4(7H_2O)$, 11 mg/L $CaCl_2(2H_2O)$, 10 mg/L $MnCl_2(4H_2O)$, 2 mg/L, $(NH_4)_6Mo_7O_{24}(4H_2O)$, 2.4 mg/L $H_3BO_3$, 50 mg/L EDTA; 0.01 g/L each of growth factors adenine, cytosine, guanine, uracil, thymine; 0.5 mg/L each of vitamins thiamine, riboflavin, calcium pantothenate, niacin, pyridoxamine, thioctic acid; 0.5 mg/L each of vitamins folic acid, biotin, $B_{12}$; 15 g/L Difco vitamin-free casamino acids, 0.15 g/L tryptophan, 0.6 g/L cysteine, and 15 g/L glucose. Macro minerals, amino acids, glucose, and acidified purines and pyrimidines were autoclaved separately. Vitamins and trace minerals <0.1 g/L were filter sterilized. After combining sterilized ingredient groups, pH was adjusted to 7 with NaOH.

Shake-Flask Cultivations of Bacterial Inocula for Test Cultures

Fifty-mL precultures were the source of inocula for fermentors and shake flask test cultures. Pre-cultures contained SDCL medium in 125-mL flasks, and were shaken at 250 rpm (2.5 cm eccentricity) and 25° C. in a New Brunswick Psychroterm incubator. Cultures harvested after 24 h incubation were used to supply bacteria for baffled flask or fermentor test culture inoculations. Typical cell accumulations reached ~0.5-1×10$^{10}$ per mL.

Baffled Shake-Flask Cultivations of Bacteria

Test cultures of 75-mL volume were incubated in 500-mL baffled flasks shaken at 25° C. and 250 rpm. The culture medium was the SDCL medium above enriched to contain 40 g/L glucose, 60 g/L casamino acids, 0.6 g/L tryptophan, and 2.4 g/L cysteine. Bacteria were inoculated to an initial absorbance at 620 nm of 0.1 (1×10$^8$ viable cells/mL) and harvested after 72 h of incubation. In flask co-cultures, the initial bacterial concentrations were set such that each population initially contributed equally to the overall culture absorbance, except that the $E.$ $cloacae$ S11:T:07 population in co-cultures was always set at 0.0001 since this strain could exclude the other three $P.$ $fluorescens$ strains if inoculated to higher levels.

Fermentor Cultivations of Bacteria

Bacteria were cultivated in 2-L B. Braun Biostat B or ED fermentors charged with 1.6 L of the SDCL medium above enriched to contain 40 g/L glucose, 0 g/L casamino acids, 0.6 g/L tryptophan, and 2.4 g/L cysteine. Fermentors were controlled at 25° C., pH 7 (with 6N NaOH or 3 N HCl additives), 1 L/min aeration, and variable stirring 300-1500 rpm to maintain dissolved oxygen at 30% of saturation. To control foaming, a 20% solution of Cognis FBA 3107 was dosed as needed. Bacteria were inoculated to an absorbance at 620 nm of 0.1 (1×10$^8$ viable cells/mL) and harvested after growth 72 h; at which time, viable cell accumulations were typically ~2-3×10$^{10}$ per mL, giving an absorbance of ~20. Fermentor co-cultures of $Pseudomonas$ $fluorescens$ strains were inoculated to have the following initial absorbances, unless otherwise specified: 0.05 for each of S22:T:04 and S11:P:12 and 0.01 for P22:Y:05.

Enumeration of Mixed Bacteria Populations Using Selective Plating Media

Total bacterial biomass (b) was assessed using absorbance at $A_{620}$ where b=kA and k=0.408 g/L per absorbance unit assuming a 1 cm path length (Slininger and Jackson. 1992. Nutritional factor regulating growth and accumulation of phenazine 1-carboxylic acid by $Pseudomonas$ $fluorescens$ 2-79. Applied Microbiology and Biotechnology 37:388-392). The viable cell concentrations of each population in mixed cultures or blends were assessed by dilution plating cultures in duplicate to each of three selective agar media: King's Medium (KMB), ⅕ TSA plus Tetrazolium (TSA-T), and Minimal Medium with Histidine and Tetrazolium (MMHT). Total counts of all strains as well as S11:P:12 were obtained from TSA-T spread plates after 24-48 h incubation at 25° C., Strain S11:P:12 formed a distinctively large diameter diffuse shiny colony becoming creamy with a pink concentric rings (2-5 mm). Other strains formed smaller dense round colonies (1-2 mm) with red centers and white borders. A selective count of P22:Y:05 as deep red colonies, white edges (1 mm) was obtained from MMHT spread plates after incubation 48-72 hours, while colonies of the other strains used in the study remained relatively tiny and white. The plating tool for P22:Y:05 was developed using Biolog GN plates to screen carbon sources used by the four bacteria, allowing discovery of histidine as a selective carbon source. A specific count of $Enterobacter$ $cloacae$ S11:T:07 was determined by picking 30 random non-S11:P:12 colonies from each countable TSA-T plate to KMB plates where the percentage of non-fluorescing colonies could be evaluated. Non-fluorescent colonies on KMB were $E.$ $cloacae$, whereas fluorescent colonies were either $P.$ $fluorescens$ P22:Y:05 or S22:T:04.

Plating medium ingredients in the ⅕ TSA-T were: 6 g/L Difco Bacto Tryptic Soy Broth, 15 g/L Difco Bacto Agar, and 0.05 g/L 2,3,5-triphenyl-tetrazolium chloride (tetrazolium red, T-8877, Sigma). The medium was prepared by mixing the TSB and agar in distilled water, autoclaving, then mixing in 10 mL of tetrazolium filter-sterilized concentrate to the ~60° C. agar mix. Solidified plates were refrigerated to preserve the tetrazolium red.

Ingredients in the MMHT were the following: 2 g/L $K_2HPO_4$, 2 g/L $KH_2PO_4$, 0.01 g/L $FeSO_4(7H_2O)$ 0.1 g/L $MgSO4(7H_2O)$, 0.01 g/L NaCl, 0.0044 g/L $ZnSO_4$ $(7H_2O)$, 0.011 g/L $CaCl_2$ $(2H_2O)$, 0.01 g/L $MnCl_2(4H_2O)$, 0.002 g/L $(NH_4)_6MO_7O_{24}(4H_2O)$, 0.024 g/L $H_3BO_3$, 0.05 g/L EDTA, 1.26 g/L urea, 5 g/L hisitidine, 15 g/L BD Difco agar, and 0.05 g/L 2,3,5-triphenyl-tetrazolium chloride. The MMHT was prepared by mixing warm, double-strength autoclaved agar with the double-strength filter-sterilized nutrient solution and tetrazolium concentrate in a sterile bottle with stir bar. The MMHT nutrient solution preparation was done similarly to the SDCL fermentation medium described above and adjusted to pH 7 before mixing with the agar solution. The medium was poured to plates immediately upon mixing, and the solidified plates, as for TSA-T, were stored refrigerated.

Ingredients in King's Medium B were: 10 q/L BD Difco Bacto Proteose Peptone#3, 10 g/L glycerol, 1.5 g/L $K_2HPO_4$, 1.5 g/L $MgSO_4(7H_2O)$, and 15 g/L BD Difco Bacto Agar. KMB ingredients were mixed, pH adjusted to 7.2, autoclaved and then molten agar was poured to plates.

Peoria Wounded Potato Bioassay of $Fusarium$ Dry Rot or Pink Rot Suppression

The wounded potato bioassay of treatment efficacy against $Gibberella$ $pulicaris$ (Fr.:Fr.) Sacc. (anamorph: $Fusarium$ $sambucinum$ Fuckel) strain R-6380 was originally described in Schisler and Slininger (1994. ibid). In the present study, the bacteria treatments were diluted by mixing 0.5 mL culture with 17.5 mL of chilled buffer, and then 1:1 (v/v) with $G.$ $pulicaris$ R-6380 at either 1 or 3×10$^6$ conidia/mL (by hemacytometer count), pending virulence in prior assays. Potato wounds made with a 2 mm diameter×2 mm length steel pin were thus co-inoculated with treatment and pathogen by pipetting 5 μL of the 1:1 (v/v) treatment:pathogen mixture to each wound. Each bacteria treatment was repeated on six size B Russet Burbank seed potatoes (Wisconsin Seed Potato Certification Program, University of Wisconsin Madison, Antigo, Wis.) that had been washed and dried a day ahead at room temperature, following prior storage in a cold room ~4° C. Each potato had four wounds equally spaced around the middle-three wounds receiving bacteria and pathogen and one control wound receiving only pathogen mixed with buffer controls. Each potato was placed in a plastic weigh boat on a dry 2.54 cm-cut square of Wyp-all L40 all purpose wiper paper towel (Kimberly-Clark Worldwide, Inc.). Boats were held in trays that were supplied two dry Wyp-alls over the top of potatoes and two Wyp-alls wet with 40 mL of water each and placed on either side of the tray, plastic bagged, and stored 21 days at >90% relative humidity and 15° C. After storage each potato was quartered, slicing through the center of each of the four wounds. The extent of disease in each wound was rated by adding the greatest depth and width measurements (mm) of discolored necrotic tissue extending below and to the sides of the wound. Relative disease (%) was calculated as 100×(wound disease rating/average disease rating of wounds receiving pathogen only).

Similarly, pink rot suppression was assayed on wounded potatoes. Zoospores of the causative pathogen $Phytophthora$ $erythroseptica$ strain 02-05 were produced per Schisler et al. (2009. Bacterial antagonists, zoospore inoculums retention time and potato cultivar influence pink rot disease development. American Journal of Potato Research 86:102-111) and suspended at $3\times10^4$ zoospores/mL buffer before mixing 1:1 with biocontrol a gent treatments (or buffer control). Then 5 µL of each treatment-pathogen mixture was applied to 10 replicate wounds, each wound on a different potato. Each potato had two wounds and was used to test two treatments. Tubers were stored as for the dry rot assay, and pink rot development was rated after one week, using the same lesion width plus depth method as described above for dry rot.

Kimberly Small Pilot Evaluations of Biocontrol Efficacy-Late Blight, Pink Rot, Sprouting Late Blight

*Phytophthora infestans* JMUIK-2002 (US-8, mating type A2) was obtained from Dr. Jeff Miller (University of Idaho, Aberdeen, Id.) for small pilot testing of disease suppression under commercial storage conditions at the University of Idaho Kimberly Research and Extension Center, Kimberly, Id. Kimberly rye agar plates were grown in darkness for 2 weeks at 18° C., where rye agar was prepared as follows: 60 g rye seed were soaked over night; seeds were then ground in blender 3 min and strained out using four layers cheesecloth; deionized water was poured through pulp until 1 L total volume suspension was collected; 10 g glucose and 15 g agar were added just prior to autoclaving. Plates were harvested by adding 10 mL of ~4° C. water per plate and scraping with a glass hockey stick to recover about 9 mL containing $2\times10^5$ sporangia/mL. For tuber inoculation, 2.5 L of $4\times10^4$ sporangia/mL were chilled 1.5 h and then warmed to room temperature ~15-18° C. for 45 minutes to liberate zoospores.

The suspension of *P. infestans* was sprayed onto all of the tubers for the trial at a rate of 1.6 mL per 8 oz. tuber (0.8 mL/tuber first to one side plus 0.8 mL/tuber to the other side). An air-assist syringe sprayer was used with a Delevan brass nozzle (#4, 80° LF.). The sprayer and nozzle were sterilized between treatments by rinsing once with 70% ethanol and then three times with distilled water. Potatoes were sprayed in groups of about one hundred spread out on plastic sheeting which could be drawn up to cover the potatoes to retain moisture until the bacterial treatments or water controls were applied. Pathogen-inoculated potatoes were collected into three replicate groups, and allowed to set no more than 45 minutes prior to treatment with biocontrol agents. Bacterial cultures were harvested from fermentors and stored refrigerated or in chilled shipping coolers 2-5 days before the trial. On the day of the trial, cultures were diluted in half with cold distilled water and returned to the refrigerator until application. Each bacterial treatment or water control treatment was then similarly sprayed at a rate of 0.8 mL per tuber to 30 potatoes from each of the three pathogen-treated replicate groups.

Each treatment replicate of 30 tubers was placed in a unventilated plastic box with lid and positioned randomly on shelves in the storage bay which was maintained at 7.2° C. (45° F.) and 95% relative humidity. After four weeks storage, potatoes were peeled and rated based on the percentage of surface area showing the discoloration typical of late blight infection.

Pink Rot

*Phytophthora erythroseptica* strain 01-21, the causative pathogen of pink rot disease, was produced by Mr. Shane Clayson and Dr. Jeff Miller (University of Idaho, Aberdeen, Id.) (Schisler et al. 2009 ibid). To release zoospores, plates were chilled on ice one hour and then allowed to warm to room temperature for 2 hours. To prepare pathogen inoculum to be used in each trial, around 50 plates of *P. erythroseptica* (Pe) were harvested at a rate of about $5\times10^5$ zoospores/10 mL distilled water per plate.

Russet Burbank tubers were bruised by tumbling about 75 tubers at a time for two minutes in a padded plastic cement mixer. Enough tubers were bruised to accommodate 4 reps of 15 tubers per each treatment. Pe suspension ($10^4$-$10^5$ zoospores/mL pending virulence) was sprayed onto tubers at a rate of 1.6 mls per 8 oz Russet Burbank or Russet Norkota tubers. Seventy-five tubers at a time were placed on a plastic sheet-covered spray table, and 60 mls were applied to the first side of the potatoes. Tubers were flipped and 60 more mls were applied to the other side, for a total of 120 mL per 75 tubers, or 1.6 mL per tuber. Tubers were then taken off the table using the plastic sheet, set on the cement floor (~60-65° F.) and the edges pulled up to completely cover the tubers and retain moisture. This process was repeated to prepare four pools of bruised, pathogen treated tubers, such that one 15-tuber replicate of each treatment was drawn from each of the four pools. Before experimental bacterial treatments were applied, tubers were left for approximately 15 minutes after the final rep of each cultivar was treated with pathogen. This process was then repeated in its entirety for the Russet Norkota tubers after bacterial inoculation of the Russet Burbank cultivar was complete.

Bacterial treatments and water controls were applied at a rate of 0.8 mL per tuber. As for the late bight evaluation, ready-to-spray bacterial treatments were prepared and set aside in the refrigerator for plating at the end of the day. To form each treatment rep, 15 tubers from each of the four plastic sheets on floor were placed onto spray table, marking the replicate origin. To one side of the 60 potatoes, 24 mls were applied to the 60 tubers, and then another 24 mls were applied after the tubers were flipped. Tubers were then placed into their respective rep bags at 15 tubers per bag and then all 4 rep bags placed in the appropriate box. Boxes were then moved immediately into storage bay and a lid placed on the box. No ventilation was connected to the boxes. The process was then repeated with Russet Norkota being treated with pathogen, 15 minutes wait, then bacterial treatments.

Treatment boxes were stored at 17° C. for 3 weeks to allow disease development. At the end of the storage period, potatoes were rated by peeling and evaluating the percentage of surface coverage by lesions typical of pink rot.

Sprouting

Biological control treatments and water only control were sprayed at. 0.8 mL per 8 oz Russet Burbank potato. For each treatment, three replicate groups of 70 potatoes were sprayed. Each replicate was spread over a plastic sheet-covered table and sprayed with half the volume on one side, flipped, and then the other half of the volume was sprayed to the other side. Each replicate was transferred to a plastic box labeled with treatment and replicate numbers. The plastic sheet was toweled off to minimize excess collection of treatment on the plastic between spraying each replicate and disposed after each treatment was finished. Each box of potatoes was placed randomly in the storage, which was held at 45° F. and 95% relative humidity with 1 cfm/cwt air circulation. Ready-to-spray treatment samples were refrigerated until plating after finishing all treatment applications. Treatments were monitored by drawing 20 tubers per replicate box and measuring longest sprout per tuber, ten-potato total sprout length and ten-potato total sprout weight per replicate sampled. Potatoes were stored in November and finally monitored in April.

Statistical Analysis

Analysis of variance (ANOVA) was performed using Sigmastat 2.03 (SPSS, Inc.) to determine significant min effects and interactions of the variables tested. Pair-wise comparisons were made using Student Newman Keuls (SNK) or Least Significant Difference (LSD) analysis. The significance criterion applied was generally $P \leq 0.05$, or otherwise noted in the 0.1 to 0.001 range.

Results and Discussion

In both laboratory and small pilot testing of bioefficacy, co-cultured microbial biocontrol strains consistently outperformed pure stains and blends of strains produced individually in pure cultures.

Co-Culture Versus Blend Efficacy for all Combinations of Four Strains Grown in Baffled Flasks In this experiment design all 4-, 3-, and 2-strain combinations as well as pure strains S11:P:12, S22:T:04, P22Y:5, and S11:T:07 were inoculated to baffled flask cultures. The co-culture and pure culture populations harvested after 72 h had the strain compositions and absorbances listed in Table 7. Pure stain cultures were blended in equal volume to Form the "blend" compositions listed. These treatments were tested in two dry rot wounded potato bioassay experiments, one at $0.5 \times 10^6$ F. sambucinum conidia/mL and another experiment at $1.5 \times 10^6$ conidia/mL per 5 µL wound. The impact of strain composition versus combination method on Fusarium dry rot disease development (percent relative disease) was tested and analyzed using two-way analysis of variance.

Selective plating media not requiring antibiotic markers were designed and used since preliminary experiments indicated that marked strains had the complications of growth rates and potentially metabolisms being different from parent strains and phenotype drift occurring in the absence of antibiotic pressure. A nutrient-based selective plating scheme was chosen to monitor the individual strain populations in co-cultures, allowing results directly representing the natural biocontrol strains and their kinetic characteristics.

Disease ratings observed in wounded potatoes bioassays indicated that all biocontrol agent treatments, including co-cultures, blends, and pure cultures significantly reduced dry rot disease development relative to both low and high level pathogen challenges ($P<0.001$) Since the treatment×pathogen level interaction was not significant, the two pathogen level data sets were combined for further analysis. Subsequent two-way analysis of variance of relative disease with strain composition of treatments by the method of combining strains (blend versus co-culture) showed that significantly better Fusarium dry rot suppression was obtained by co-cultures than by similar strain mixtures created by blending pure strain cultures ($P<0.001$) (Table 6). The mean relative disease rating ($\pm$the standard error) for blended strain combinations was $41.3 \pm 2.4\%$, while only $30.3 \pm 2.4\%$ for co-cultures, indicating that co-cultures reduced disease to a greater extent (69.7%) than had the blended strain combinations (58.7%). Using a $P<0.05$ significance criterion, the variation of relative disease among the various strain compositions was not significant ($P=0.082$) nor was the composition×combination method interaction ($P<0.0.76$).

An analysis was also done to determine whether biocontrol strain populations in co-cultures and blends were performing additively or synergistically co-culture refers to the technique of cultivating multiple strains together in one fermentation vessel starting from a low initial cell population density that multiplies and advances through growth phase to stationary phase. This process contrasts with blending large populations of strains together after they are grown separately as pure strain cultures from low initial cell concentration through growth phase to stationary phase. When strain populations are grown together prior to application, they may have the opportunity to stimulate one another in such a way as to provide a final mixed population that suppresses disease more efficiently than a blend of pure cultures. On the other hand, co-cultured strains may not be compatible with one another, such that low population concentrations result or the end product does not suppress disease as well as observed for pure strains or a blend of pure strains. To test positive versus negative impact of strain combinations, the expected relative disease rating was calculated for comparison with the actual disease rating measured for each treatment comprised of multiple strains: $RDR_{calc}=(RDR_1 \times N_1 + RDR_2 \times N_2 + RDR_3 \times N_3 + RDR_4 \times N_4)/(N_1+N_2+N_3+N_4)$, where $N_1$ is the concentration of strain population 1 (such as S11:P:12 viable cells/mL) in a multiple strain mixture and $RDR_1$ is the relative disease rating observed for the pure strain population 1, and so forth for strains 2 through 4. Thus, $RDR_{calc}$ for a mixed population is a population-weighted average of the observed disease ratings for single-strain treatments; or in other words, it is addition of the fractional performance contributions of each component strain. Comparison of $RDR_{calc}$ with actual disease ratings of strain blends and co-cultures will indicate if the efficacy of strain components of a mixture are additive or if the method of combining them provides a synergistic advantage or disadvantage or disadvantage relative to the disease suppressiveness observed for pure strains applied individually.

After 72-h incubation both pure and co-cultures accumulated virtually the same biomass concentration as indicated by culture absorbances averaging $16.0 \pm 0.88$ and $15.9 \pm 1$, respectively Table 7). In co-cultures containing E. cloacae strain S11:T:07, it was the dominant population in 72-h cultures, but low concentrations of other strains also existed. In co-cultures without E. cloacae, the 72-h populations were more equally divided among the P. fluorescens strains present. Nearly all co-cultures, regardless of the population distribution among strains, exhibited lower disease levels than expected by calculation of $RDR_{calc}$ from the additive performance contributions of pure strains, The mean actual relative disease rating ($\pm$standard deviation) for co-cultures ($30.3 \pm 6.3\%$) was significantly lower than both the mean co-culture $RDR_{calc}$ and the mean actual relative disease rating for blends, $42.9 \pm 5.3\%$ and $41.3 \pm 13.1\%$, respectively. In contrast, the mean actual relative disease rating for blends ($41.3 \pm 13.1\%$) was similar to that of pure strains ($39.9 \pm 6.6\%$) as well as the predicted mean value of $RDR_{calc}$ for blends ($40 \pm 2.8\%$) obtained by adding the efficacy contributions of pure strains. These findings provide evidence that co-culturing strains stimulates synergistic inter-strain activities that boost biocontrol efficacy. This synergy is apparently not developed in strains that are grown separately and mixed just prior to addition to potato wounds.

Consistency of Co-Culture, Blend and Pure Strain Biocontrol Treatment Efficacy Across Lab Bioassays and Small Scale Commercial Storage Simulation In the investigation of the various strain combinations grown in baffled flasks, final treatment populations were not always equally distributed among the component strains in co-cultures where variable growth kinetics of strains occurred (Table 7). Similar populations in three strain mix fermentations after 72-h cultivation were achievable in fermentors by inoculating faster growing population P22:Y:05 to lower initial cell density than slower growing P. fluorescens strains S22:T:04 and S11:P:12 (FIG. 1). The performance of this three-strain co-culture was compared versus pure strains and the corresponding three-strain blend comprised of an equal volume mix of the three pure-strain populations grown under the same fermentor conditions. These treatments were compared in sixteen experiments conducted in laboratory experiments in Peoria using wounded potato bioassays of dry rot or pink rot suppressiveness or in Kimberly, Id. using small pilot simulations of commercial storage conditions during challenges of late blight, pink rot, and sprouting. The performance of treatments was then ranked within each experiment by calculating the dimensionless relative performance index of each treatment. Overall treatment performance could then be assessed and analyzed using analysis of variance and pairwise comparison techniques to determine superior treatments.

Tables 1A and 1B show the average strain populations in ready-to-apply treatments for the 16 laboratory and small pilot experiments as measured by dilution plating on selective media. These data show that co-culture, blend and pure strain treatments had similar total cell concentrations, and that blend and co-culture treatments had similar strain distributions. Table 2 summarizes the performance of the treatments in nine small-scale pilot tests in Kimberly, Id. simulating commercial storage conditions. Table 3 summarizes the performance of similar treatments applied in seven laboratory experiments conducted in Peoria, Ill. using the wounded potato bioassay. Scanning these data, it is evident that at least one and usually more biocontrol treatments significantly reduced disease or sprouting relative to the control. Co-culture had a lower mean disease rating than the blend in 9 of 16 experiments. The co-culture led other treatments in incidence of successful significant disease or sprout reduction relative to the control: 14 of 16 attempts for co-culture, 11 of 16 attempts for blend, 10 of 13 attempts for S11:P:12, 8 of 13 attempts for S22:T:04, and 9 of 13 attempts for P22:Y:05.

For each bacterial and control treatment within an experiment, a relative performance index (RPI) was calculated, as listed in brackets to the right of means in Tables 2 and 3. RPI is a dimensionless value that is useful in combining data sets to use in overall ranking or statistical analysis of treatments submitted to various testing procedures. Given disease or sprout ratings normally distributed across the group of bacteria stains tested, the value of $F=(X-X_{avg})/s$ ranges from $-2$ to $+2$. Here, X designates a disease or sprout rating observed per treatment, and $X_{avg}$ and s are the average and standard deviation, respectively, of all values observed for the group of bacteria treatments within a given experiment, such as the fall 2005 late blight bioassay at Kimberly. Since F decreases as disease or sprout suppressiveness improves, then $RPI=(2-F)\times100/4$, such that the value of RPI ranges from ~0 to 100 percentile from least to most suppressive, respectively.

A one-way analysis of variance of RPI by treatment showed significant efficacy of biocontrol agents to suppress potato maladies relative to the control (Table 4). However, high standard deviation prevented statistical separation of the performances of biocontrol treatments although co-culture treatments performed most consistently across all sixteen assays as indicated by exhibiting the highest overall mean RPI and the lowest relative standard deviation. A two-way analysis of variance in RPI with treatment and malady was performed which considered co-culture, blend and control across all sixteen experiments conducted in Kimberly and Peoria. The result of this analysis is given in Table 5 and indicates that the overall mean RPI for the co-culture treatment was significantly higher than that for the blend.

It is understood that the foregoing detailed description is given merely by way of illustration and that modifications and variations may be made therein without departing from the spirit and scope of the invention.

TABLE 1

Average biocontrol strain populations applied in treatments

A. Peoria laboratory wounded potato bioassays

| Treatment | Average Population Concentration × $10^{-8}$ (cells/mL)[a,b] | | | |
|---|---|---|---|---|
| | S11:P:12 | S22:T:04 | P22:Y:05 | Total |
| Co-culture | 0.63 ± 0.15 B | 1.49 ± 0.84 B | 0.61 ± 0.55 B | 2.72 ± 0.85 A |
| Blend | 0.56 ± 0.34 B | 0.84 ± 0.25 B | 0.86 ± 0.26 B | 2.26 ± 0.49 A |
| S11:P:12 | 1.61 ± 0.74 A | 0 | 0 | 1.61 ± 0.74 A |
| S22:T:04 | 0 | 2.60 ± 1.55 A | 0 | 2.60 ± 1.55 A |
| P22:Y:05 | 0 | 0 | 2.28 ± 1.19 A | 2.28 ± 1.19 A |
| Control | 0 | 0 | 0 | 0 |

B. Kimberly small pilot bioassays simulating commercial storage conditions

| Treatment | Average Population Concentration × $10^{-9}$ (cells/mL)[a,b] | | | |
|---|---|---|---|---|
| | S11:P:12 | S22:T:04 | P22:Y:05 | Total |
| Co-culture | 2.22 ± 0.88 B | 2.01 ± 2.8 B | 4.52 ± 2.24 B | 8.76 ± 3.50 B |
| Blend | 1.48 ± 0.64 B | 1.47 ± 1.40 B | 2.39 ± 0.76 B | 5.35 ± 2.72 BC |
| S11:P:12 | 3.65 ± 1.86 A | 0 | 0 | 3.65 ± 1.86 C |
| S22:T:04 | 0 | 12.3 ± 1.5 A | 0 | 12.3 ± 1.5 A |
| P22:Y:05 | 0 | 0 | 7.24 ± 5.70 A | 7.24 ± 5.70 BC |
| Control | 0 | 0 | 0 | 0 |

[a]Within columns, values not sharing a similar letter are significantly different based on Student-Newman-Keuls pairwise comparison method using P < 0.05 significance criterion.
[b]Standard deviations in mean values are indicated following the "±" symbol.

TABLE 2

Summary of treatment performance in Kimberly, Idaho small pilot tests simulating commercial storage Late Blight (% Surface Coverage)[e,h]

| Treatment | Fall 2005 | | Winter 2006 | | Winter 2007 | | Fall 2007 | | Winter 2008 | |
|---|---|---|---|---|---|---|---|---|---|---|
| Coculture | 29.4[81] | A | 6.7[60] | AB | 6.3[84] | A | 12.1[68] | A | 2.50[51] | A |
| Blend | 45.3[49] | B | 5.8[74] | A | 11.2[40] | AB | 13.4[55] | A | 1.85[60] | A |
| S11:P:12 | — | — | — | — | 6.9[78] | A | 15.4[34] | A | 1.63[63] | A |
| S22:T:04 | — | — | — | — | 11.1[41] | AB | 11.9[70] | A | 1.39[66] | A |
| P22:Y:05 | — | — | — | — | 10.5[47] | AB | 11.7[72] | A | 1.52[65] | A |
| Control[d] | 59.4[20] | C | 9.5[16] | B | 14.7[10] | B | 18.6[2] | B | 6.38[−5] | B |
| Significance | $P < 0.05$ | | $P < 0.075^a$ | | $P < 0.05^a$ | | $P < 0.1^a$ | | $P < 0.05^a$ | |

Pink Rot (% Surface Coverage)[f,h]

| Treatment | Winter 2007[g] | | Winter 2008 RB | | Winter 2008 RN | |
|---|---|---|---|---|---|---|
| Co-culture | 50.8[54] | AB | 66.3[53] | AB | 90.8[69] | A |
| Blend | 48.6[60] | AB | 59.3[73] | A | 89.3[80] | A |
| S11:P:12 | 40.9[81] | A | 75.8[26] | BC | 92.2[58] | A |
| S22:T:04 | 53.8[46] | B | 59.8[72] | A | 95.1[37] | AB |
| P22:Y:05 | 48.6[60] | AB | 60.8[69] | A | 92.8[54] | A |
| Control[d] | 70.6[0] | C | 82.5[7] | C | 99.8[2] | B |
| Significance | $P < 0.05^b$ | | $P < 0.05^b$ | | $P < 0.1^c$ | |

| Treatment | Sprout Weight (%)[h] Fall 2005-April 2006 | |
|---|---|---|
| Co-culture | 0.438[80] | A |
| Blend | 0.603[51] | AB |
| Control[d] | 0.788[19] | B |
| Significance | $P < 0.05^a$ | |

[a]Within the column, values having no letters in common are significantly different based on Student-Newman-Keuls pairwise comparison test.
[b]Within the column, values having no letters in common are significantly different based on Fisher's Protected LSD test using arcsine transformation if needed to normalize data.
[c]Values not sharing a similar letter are significantly different based on an unprotected LSD test.
[d]The control treatment consists of water instead of biocontrol agent applied to potatoes infested with pathogen.
[e]Late blight is incited by $4 \times 10^4$ sporangia/mL *Phytophthora infestans* sprayed at 1.6 mL per 8 oz Russet Burbank tuber.
[f]Pink rot is incited by $10^4$-$10^5$ zoospores/mL, pending virulence, *Phytophthora erythroseptica* sprayed at 1.6 mL per 8 oz Russet Burbank (RB) or Russet Norkota (RN) tubers.
[g]Data represent combined means of Russet Burbank and Russet Norkota data sets since no significant treatment x cultivar interactions.
[h]Each number in brackets indicates the corresponding relative performance index (RPI) of the value relative to other data within the experiment column.

TABLE 3

Summary of treatment performance in Peoria laboratory wounded potato bioassays

Dry Rot Disease Rating (mm)[a,g]

| Treatment | Fall 2006[e] | | Winter 2007[e2] | | Spring 2007A[e] | | Spring 2007B[e] | | Fall 2007[e2] | |
|---|---|---|---|---|---|---|---|---|---|---|
| Co-culture | 5.3[63] | A | 5.2[71] | A | 23.0[62] | A | 28.7[77] | A | 6.7[62] | A |
| Blend | 6.2[59] | A | 5.5[71] | A | 27.7[53] | A | 27.2[82] | A | 6.2[64] | A |
| S11:P:12 | 4.5[63] | A | 9.3[64] | A | 27.8[52] | A | 35.0[53] | AB | 9.0[54] | A |
| S22:T:04 | 3.2[65] | A | 19.3[46] | A | 16.3[75] | A | 35.3[52] | AB | 6.8[62] | A |
| P22:Y:05 | 7.2[57] | A | 17.8[49] | A | 23.3[61] | A | 44.1[19] | AB | 6.0[64] | A |
| Control[d] | 37.6[−6] | B | 46.1[−1] | B | 56.3[−3] | B | 44.2[18] | B | 26.9[−5] | B |
| Significance | $P < 0.001^b$ | | $P < 0.001^b$ | | $P < 0.001^b$ | | $P < 0.05^b$ | | $P < 0.001^b$ | |

Pink Rot Disease Rating (mm)[a,f,g]

| Treatment | Fall 2006 | | Winter 2007 | |
|---|---|---|---|---|
| Co-culture | 54.5[39] | AB | 19.5[83] | A |
| Blend | 57.9[24] | B | 23.4[45] | ABC |
| S11:P:12 | 43.3[89] | A | 20.0[78] | ABC |
| S22:T:04 | 53.2[44] | AB | 26.9[11] | C |
| P22:Y:05 | 45.7[78] | AB | 23.0[49] | ABC |

TABLE 3-continued

Summary of treatment performance in Peoria laboratory wounded potato bioassays

| Control[d] | 57.7[25] | B | 24.6[33] | BC |
|---|---|---|---|---|
| Significance | $P < 0.1^c$ | | $P < 0.1^c$ | |

[a]Disease ratings represent lesion width plus depth around a wound.
[b]Values not sharing a similar letter are significantly different based on Student-Newman-Keuls Method pairwise comparison method.
[c]Values not sharing a similar letter are significantly different based on an LSD all pairwise comparisons test applied to the disease ratings.
[d]The control treatment consists of water + pathogen only applied to potatoes infested with pathogen.
[e]Dry rot is incited by $0.5 \times 10^6$ conidia *Fusarium sambucinum* per mL pipetted 5 μmL per wound on Russet Burbank potatoes.
[e2]Dry rot is incited by $1.5 \times 10^6$ conidia *Fusarium sambucinum* per mL pipetted 5 μmL per wound on Russet Burbank potatoes.
[f]Pink rot is incited by $1.5 \times 10^4$ zoospores *Phytophthora erythroseptica* pipetted 5 μmL per wound. Data represent combined means of Russet Burbank and Russet Norkota data sets for each treatment.
[g]Each number in brackets indicates the corresponding relative performance index (RPI) of the value relative to other data within the experiment column.

TABLE 4

One-way analysis of variance by treatment shows significant efficacy of biocontrol agents to suppress potato maladies relative to the control, but high standard deviation prevents performance differentiation when interactions of treatment by potato malady type are ignored. Co-culture treatments perform most consistently across all sixteen assays with lowest relative standard deviation.

| Treatment | Mean RPI[a] | | Standard Deviation In Mean RPI | Relative Standard Deviation (%) |
|---|---|---|---|---|
| Co-culture | 65.9 | A | 13.1 | 19.8 |
| Blend | 58.7 | A | 15.4 | 26.2 |
| S11:P:12 | 61.1 | A | 18.1 | 29.6 |
| S22:T:04 | 52.9 | A | 17.9 | 33.8 |
| P22:Y:05 | 57.2 | A | 14.9 | 26.0 |
| Control | 8.2 | B | 12.2 | 148.7 |

[a]Within the column, means not sharing a similar letter are significantly different based on the Student-Newman-Keuls pairwise comparison method ($P < 0.05$ significance criterion).

TABLE 5

Two-way analysis of variance of Relative Performance Index (RPI) with treatment x malady indicated that the relative biocontrol performance of the co-culture treatment was significantly better than that of the blend treatment over all sixteen experiments conducted in Kimberly and Peoria.

| Treatment | Potato Malady Bioassay | Average RPI Treatment x Malady[a] | Average RPI for Treatment Groups[a,b] | |
|---|---|---|---|---|
| Co-culture | Late Blight | 68.7 ± 6.2 | 68.7 ± 4.4 | A |
| | Pink Rot | 59.6 ± 6.2 | | |
| | Dry Rot | 66.5 ± 6.2 | | |
| | Sprouting | 80.0 ± 13.9 | | |
| Blend | Late Blight | 55.6 ± 6.2 | 57.2 ± 4.4 | B |
| | Pink Rot | 56.4 ± 6.2 | | |
| | Dry Rot | 65.7 ± 6.2 | | |
| | Sprouting | 51.2 ± 13.9 | | |
| Control | Late Blight | 8.5 ± 6.2 | 10.3 ± 4.4 | C |
| | Pink Rot | 18.8 ± 6.2 | | |
| | Dry Rot | 13.5 ± 6.2 | | |
| | Sprouting | 0.5 ± 13.9 | | |

[a]Least square means are reported, and the standard error in the means is given following each "±" symbol.
[b]Within the column, values having no letters in common are significantly different based on Student-Newman-Keuls pairwise comparison test using the $P < 0.075$ significance criterion.

TABLE 6

Two-way analysis of variance of relative disease with strain composition of treatments and method of combining strains showed that significantly better *Fusarium* dry rot suppression was obtained by strain co-cultures than by similar strain mixtures created by blending pure strain cultures.

| Treatment Composition of Strains Strain Presence (1) Absence (0) | | | | Least Square Mean of Relative Disease (%)[a,b] | |
|---|---|---|---|---|---|
| *Pseudomonas fluorescens* S11:P:12 | *Pseudomonas fluorescens* S22:T:04 | *Pseudomonas fluorescens* P22:Y:05 | *Enterobacter cloacae* S11:T:07 | Strain Combination Method | |
| | | | | Co-culture | Blend |
| 1 | 1 | 1 | 1 | 28.2 | 25.4 |
| 1 | 1 | 1 | 0 | 39.8 | 30.8 |
| 1 | 0 | 1 | 1 | 39.8 | 50.5 |
| 1 | 1 | 0 | 1 | 30.7 | 34.3 |
| 0 | 1 | 1 | 1 | 22.5 | 45.5 |
| 1 | 0 | 1 | 0 | 25.0 | 44.8 |
| 1 | 1 | 0 | 0 | 26.7 | 30.0 |
| 1 | 0 | 0 | 1 | 36.8 | 32.2 |
| 0 | 1 | 1 | 0 | 23.5 | 48.0 |
| 0 | 0 | 1 | 1 | 27.1 | 40.6 |
| 0 | 1 | 0 | 1 | 33.1 | 71.9 |

TABLE 6-continued

Two-way analysis of variance of relative disease with strain composition of treatments and method of combining strains showed that significantly better *Fusarium* dry rot suppression was obtained by strain co-cultures than by similar strain mixtures created by blending pure strain cultures.

| Treatment Composition of Strains Strain Presence (1) Absence (0) | | | | Least Square Mean of Relative Disease (%)[a,b] | |
|---|---|---|---|---|---|
| *Pseudomonas fluorescens* S11:P:12 | *Pseudomonas fluorescens* S22:T:04 | *Pseudomonas fluorescens* P22:Y:05 | *Enterobacter cloacae* S11:T:07 | Strain Combination Method | |
| | | | | Co-culture | Blend |
| Overall Least Square Means ± Standard Error[b] | | | | 30.3 ± 2.4 A | 41.3 ± 2.4 B |
| Significance | | | | P < 0.001 | |

[a]All treatments were challenged with *Fusarium sambucinum* conidia at 0.5 or 1.5 × 10$^6$ per mL pipetted 5 μL per Russet Burbank potato wound. Dry rot lesions in controls without BCA had disease ratings averaging 10.5 or 13 mm, respectively pending pathogen inoculum size. Since relative disease did not vary significantly with the interaction of treatment x pathogen concentration, analysis was conducted on the combined low and high level pathogen data sets.
[b]The overall least square means of relative disease observed for strain co-cultures versus blends were significantly different (P = 0.001) based on Student-Newman-Keuls pairwise comparison method as designated by different letters. Relative disease did not vary significantly due to the strain composition of mixed strain treatments or the interaction of treatment strain composition x combination method.

TABLE 7

One-way analysis of variance of actual and calculated relative disease ratings indicate that strains grown in co-cultures develop synergistic activities that support superior disease suppressiveness compared with blends of pure strains cultivated separately.

| Strain Combination Method | 72-h Culture Viable Cell Populations × 10$^{-10}$ (cells/mL)[e] | | | | 72-h Culture Absorbance (620 nm)[a] | Actual Relative Disease Rating[a,b,c] (%) | Calculated Relative Disease Rating[a,b] (%) |
|---|---|---|---|---|---|---|---|
| | S11:P:12 | S22:T:04 | P22:Y:05 | S11:T:07 | | | |
| Co-culture | 0.25 | 0.0018 | 0.10 | 2.4 | 15.2 | 28.2 | 46.2 |
| | 0.40 | 0.56 | 1.1 | 0 | 16.4 | 39.9 | 35.9 |
| | 0.027 | 0 | 0.046 | 1.1 | 14.7 | 39.9 | 46.5 |
| | 0.16 | 0.0055 | 0 | 2.2 | 16.3 | 30.7 | 46.8 |
| | 0 | 0.038 | 0.10 | 1.8 | 16.6 | 22.5 | 46.1 |
| | 0.44 | 0 | 0.57 | 0 | 16.3 | 25.0 | 37.8 |
| | 0.29 | 1.1 | 0 | 0 | 17.4 | 26.7 | 37.3 |
| | 0.0031 | 0 | 0 | 0.23 | 17.3 | 36.9 | 47.0 |
| | 0 | 0.42 | 0.56 | 0 | 14.4 | 23.5 | 34.2 |
| | 0 | 0 | 0.017 | 2.5 | 15.5 | 27.1 | 47.0 |
| | 0 | 0.012 | 0 | 2.2 | 15.2 | 33.1 | 47.0 |
| Means | | | | | 15.9 ± 1.0 A | 30.3 ± 6.3 A, a | 42.9 ± 5.3 A, b |
| Blend[d] | 0.28 | 0.4 | 0.085 | 0.2 | | 25.4 | 40.2 |
| | 0.37 | 0.53 | 0.11 | 0 | | 30.8 | 38.4 |
| | 0.37 | 0 | 0.11 | 0.27 | | 50.5 | 43.4 |
| | 0.37 | 0.53 | 0 | 0.27 | | 34.4 | 40.9 |
| | 0 | 0.53 | 0.11 | 0.27 | | 45.5 | 38.6 |
| | 0.55 | 0 | 0.17 | 0 | | 44.9 | 41.4 |
| | 0.55 | 0.80 | 0 | 0 | | 30.0 | 39.0 |
| | 0.55 | 0 | 0 | 0.40 | | 32.2 | 45.3 |
| | 0 | 0.80 | 0.17 | 0 | | 48.0 | 35.2 |
| | 0 | 0 | 0.17 | 0.40 | | 40.6 | 42.9 |
| | 0 | 0.80 | 0 | 0.40 | | 71.9 | 39.4 |
| Means | | | | | | 41.3 ± 13.1 B, a | 40.4 ± 2.8 A, a |
| Pure | 1.1 | | | | 16.4 | 44.0 | 44.0 |
| | | 1.6 | | | 14.7 | 35.6 | 35.6 |
| | | | 0.34 | | 16.3 | 33.1 | 33.1 |
| | | | | 0.8 | 16.6 | 47.1 | 47.1 |
| Means | | | | | 16.0 ± 0.88 A | 39.9 ± 6.6 AB | 39.9 ± 6.6 A |

[a]Within columns, the overall relative disease or culture absorbance means ± standard deviation shown in bold for co-culture, blend and pure strain treatments are significantly different if there are no "capital" letters in common based on Student-Newman Keuls pairwise comparison with significance criterion of P < 0.05.
[b]Within rows, the overall means for actual versus calculated relative disease are significantly different if there are no "lower case" letters in common based on a paired t-test with significance criterion P < 0.05.
[c]Since relative disease did not vary significantly with treatment strain composition or treatment x pathogen concentration interactions, statistical one-way analysis of variance was conducted on the combined low and high level pathogen experiment data sets (0.5 or 1.5 × 10$^6$ *Fusarium* conidia/mL in 5 μL inoculations to Russet Burbank potato wounds). *Fusarium* dry rot lesions in controls without biocontrol agent had disease ratings averaging 10.5 or 13 mm, for low and high level disease challenge respectively, which corresponded to 100% relative disease.
[d]Viable cell concentrations of blend treatments were calculated from the pure stain plate counts reported since equal volume mixtures of pure strain cultures were prepared.
[e]Strain populations listed as 0 cells/mL were not present in the co-culture inocula, or they were not included in blends. The concentrations listed are prior to dilution 72 times for the wounded potato bioassay.

We claim:

1. A composition of bacteria produced by the process comprising:
   a) inoculating a culture medium with at least two bacteria selected from the group consisting of *Pseudomonas fluorescens* deposited at the Agricultural Research Service Culture Collection (NRRL) under deposit accession number NRRL B-21133, *Pseudomonas fluorescens* deposited at the Agricultural Research Service Culture Collection (NRRL) under deposit accession number NRRL B-21053, *Pseudomonas fluorescens* deposited at the Agricultural Research Service Culture Collection (NRRL) under deposit accession number NRRL B-21102 and *Enterobacter cloacae* deposited at the Agricultural Research Service Culture Collection (NRRL) under deposit accession number NRRL B-21050, and incubating the inoculated medium containing said bacteria under conditions effective for growth thereof and for a period of time effective to produce a co-culture of said bacteria; and
   b) recovering said co-culture.

2. The composition of bacteria of claim 1 wherein said bacteria are incubated together in said culture medium in (a) under conditions and for a period of time effective to increase the total concentration of said bacteria by at least approximately one order of magnitude.

3. The composition of bacteria of claim 1 wherein said process further comprises screening said co-culture from (b) to select for effectiveness for inhibiting fungal diseases of potatoes.

4. The composition of bacteria of claim 1 wherein said process further comprises screening said co-culture from (b) to select for effectiveness for inhibiting sprouting of potatoes.

5. A method for suppressing fungal diseases in potatoes comprising applying to whole potato tubers, potato tuber parts, or seed tubers, the composition of bacteria of claim 1 in an amount effective to reduce the level of fungi-induced disease in the potato relative to an untreated control.

6. The method of claim 5 wherein said fungi-induced disease is selected from the group consisting of *Fusarium* dry rot caused by *Gibberella pulicaris*, pink rot caused by *Phytophthora erythroseptica*, and late blight caused by *Phytophthora infestans*.

7. A method for suppressing sprouting in stored potatoes comprising applying to a potato tuber the composition of bacteria of claim 1 in an amount effective to reduce the level of sprouting in the potato tuber during storage relative to an untreated control.

* * * * *